United States Patent
Sasaki et al.

(10) Patent No.: US 9,050,038 B2
(45) Date of Patent: Jun. 9, 2015

(54) ULTRASOUND DIAGNOSIS APPARATUS

(75) Inventors: Takuya Sasaki, Nasu-machi (JP);
Tomohisa Imamura, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 1248 days.

(21) Appl. No.: 12/417,148

(22) Filed: Apr. 2, 2009

(65) Prior Publication Data
US 2009/0251461 A1    Oct. 8, 2009

(30) Foreign Application Priority Data
Apr. 8, 2008    (JP) .................................. 2008-100669

(51) Int. Cl.
| | | |
|---|---|---|
| *A61B 8/00* | (2006.01) | |
| *G06T 15/00* | (2011.01) | |
| *G06T 15/10* | (2011.01) | |
| *A61B 8/14* | (2006.01) | |
| *A61B 8/08* | (2006.01) | |
| *G06T 15/08* | (2011.01) | |
| *G06T 15/20* | (2011.01) | |
| *G06T 19/00* | (2011.01) | |
| *G01S 15/89* | (2006.01) | |

(52) U.S. Cl.
CPC . *A61B 8/14* (2013.01); *A61B 8/483* (2013.01); *G01S 15/8993* (2013.01); *G06T 15/08* (2013.01); *G06T 15/20* (2013.01); *G06T 19/00* (2013.01); *G06T 2219/008* (2013.01)

(58) Field of Classification Search
CPC .......... A61B 8/14; A61B 8/483; G06T 15/08; G06T 15/20; G06T 15/205; G06T 19/00; G06T 2219/008
USPC ............ 600/437, 443; 345/419, 427; 382/128
See application file for complete search history.

(56) References Cited

U.S. PATENT DOCUMENTS

| | | | | |
|---|---|---|---|---|
| 6,283,918 B1 * | 9/2001 | Kanda et al. | .................. | 600/441 |
| 6,450,962 B1 * | 9/2002 | Brandl et al. | ................. | 600/458 |
| 6,480,732 B1 * | 11/2002 | Tanaka et al. | ................ | 600/425 |
| 7,108,658 B2 * | 9/2006 | Brandl et al. | ................. | 600/443 |

FOREIGN PATENT DOCUMENTS

| | | |
|---|---|---|
| JP | 2004-275223 | 10/2004 |
| JP | 2009-254506 | 11/2009 |

* cited by examiner

*Primary Examiner* — Katherine Fernandez
(74) *Attorney, Agent, or Firm* — Oblon, McClelland, Maier & Neustadt, L.L.P.

(57) ABSTRACT

An ultrasound diagnosis apparatus: in conjunction with change of a projection region using an operation part, changes a viewpoint to a position where a reference cross section is in front and the changed projection region is on the back; in conjunction with change of the viewpoint using the operation part, changes a region where the reference cross section is in front and the changed viewpoint is on the back to the projection region; in conjunction with change of a scanning region using the operation part, changes the viewpoint to a position where the reference cross section is in front and the changed scanning region is on the back; in conjunction with change of the viewpoint using the operation part, changes the scanning region to a region where the reference cross section is in front and the viewpoint is on the back; and then executes rendering.

6 Claims, 9 Drawing Sheets

ULTRASOUND DIAGNOSIS APPARATUS

BACKGROUND OF THE INVENTION

1. Field of the Invention

The present invention relates to an ultrasound diagnosis apparatus that generates a projection image by rendering volume data acquired by transmission and reception of ultrasonic waves and displays the projection image.

2. Description of the Related Art

With the rapid enhancement of computation by computers in recent years, it has become possible to generate a three-dimensional moving image by rendering 4D data acquired by continuously scanning the inside of a subject, and to make a diagnosis and provide treatment based on the three-dimensional moving image. For example, as shown in Japanese Unexamined Patent Application Publication No. 2004-275223, an ultrasound diagnosis apparatus can also acquire 4D data with a two-dimensional array ultrasound probe capable of three-dimensionally transmitting and receiving an ultrasonic beam to and from a space inside a subject and generate a three-dimensional moving image by rendering the 4D data.

Rendering is creation of a projection moving image representing a three-dimensional figure by projecting a region to be rendered in a viewing direction. A rendering method is, for example, the surface display method and the volume rendering method. In the volume rendering method, voxel data of a region viewed from a viewpoint is sampled, transmission of light in accordance with opacity and reflection to the viewpoint are calculated, and a projection moving image is generated while shading is applied.

In this rendering, it is necessary to properly specify a viewpoint and a region to be rendered. Moreover, an ultrasound diagnosis apparatus configured so that a scanning region to and from which ultrasonic waves are transmitted and received is variable also needs to properly specify the scanning region. With the rapid enhancement of computation by computers in recent years, it has become easier to change the aspects of rendering, e.g., change a viewpoint, change a region to be rendered, and change a region to be scanned. When an operator inputs change of the viewpoint and the region, the ultrasound diagnosis apparatus immediately executes re-rendering and displays an image.

However, since the operation of changing the aspects of rendering has become possible, such a problem has arisen that it is impossible to display a projection moving image taken from a desired reference cross section unless the operator properly designates the viewpoint and the region to be rendered, or properly designates a region to be scanned, the viewpoint and a region to be rendered. For example, it is assumed that one region across a reference cross section is scanned and the one region is rendered in a state that a viewpoint is set so that the reference cross section is in front and the one region is on the back. If the operator changes the position of the viewpoint from the above state to the reverse side beyond the reference cross section, the rendering is executed in an aspect that a plane opposite to the reference cross section is the surface, with the result that it is difficult to observe the reference cross section from the projection image.

In other words, when performing a viewpoint changing operation, in response to the operation, the operator must perform a changing operation to scan the other region across the reference cross section, and further perform a changing operation to render the other region. If not, a projection image with a reference cross section viewed from the changed viewpoint as the surface cannot be generated.

SUMMARY OF THE INVENTION

An object of the present invention is to provide an ultrasound diagnosis apparatus that, even if some of the conditions of rendering are changed, can maintain an aspect of rendering from a viewpoint with a reference cross section set in front of a projection region, without performing a number of complicated changing operation steps in response to the change of the conditions.

In a first aspect of the present invention: a cross sectional image of a designated or predefined reference cross section is generated based on volume data acquired by transmitting and receiving ultrasonic waves to and from the inside of a subject; a projection image is generated by rendering a predetermined projection region in a predetermined viewing direction; and the cross sectional image and the projection image are displayed on a display.

When change of the projection region is inputted through an operation part, in conjunction with the change, the viewpoint is changed to a position in which the reference cross section is in front and the changed projection region is on the back, and then this changed projection region is rendered.

Further, in a second aspect of the present invention: a cross sectional image of a designated or predefined reference cross section is generated based on volume data acquired by transmitting and receiving ultrasonic waves to and from the inside of a subject; a projection image is generated by rendering a predetermined projection region in a predetermined viewing direction; and the cross sectional image and the projection image are displayed on a display. When change of the viewpoint is inputted through an operation part, in conjunction with the change, a region in which the reference cross section is in front and the changed viewpoint is on the back is changed to the projection region, and then executing a rendering process of projecting in a direction from the changed viewpoint is performed.

According to the first and second aspects of the present invention, it is possible to maintain an aspect of rendering from the viewpoint with the reference cross section set in front of the projection region without executing a number of complicated changing operation steps such as an operation of adjusting the projection region after an operation of adjusting the viewpoint and vice versa. Therefore, grasp of a three-dimensional structure is facilitated, and the efficiency of observation of the inside of a subject is increased.

Further, in a third aspect of the present invention: a cross sectional image of a designated or predefined reference cross section is generated based on volume data of a scanning region acquired by transmitting and receiving ultrasonic waves to and from the inside of a subject; a projection image is generated by rendering the scanning region in a predetermined viewing direction; and the cross sectional image and the projection image are displayed on a display. When change of the scanning region is inputted through an operation part, in conjunction with the change of the scanning region, the viewpoint is changed to a position in which the reference cross section is in front and the changed scanning region is on the back, and then the changed scanning region is rendered.

Further, in a fourth aspect of the present invention: a cross sectional image of a designated or predefined reference cross section is generated based on volume data of a scanning region acquired by transmitting and receiving ultrasonic waves to and from the inside of a subject; a projection image is generated by rendering the scanning region in a predetermined viewing direction; and the cross sectional image and the projection image are displayed on a display. When change of the viewpoint is inputted through an operation part, in conjunction with the change of the viewpoint, the scanning region is changed to a region in which the reference cross section is in front and the changed viewpoint is on the back, and then a rendering process of projecting this scanning region in a direction from the changed viewpoint is executed.

According to the third and fourth aspects of the present invention, it is possible to maintain an aspect of rendering from the viewpoint with the reference cross section set in front of the projection region without executing a number of complicated changing operation steps, e.g., performing an operation of adjusting the position of the viewpoint and an operation of changing the projection region after an operation of changing the scanning region, or executing an operation of changing the scanning region and the projection region after changing the viewpoint. Therefore, grasp of a three-dimensional structure is facilitated, and the efficiency of observation of the inside of a subject is increased.

DETAILED DESCRIPTION OF THE EMBODIMENT

A preferred embodiment of an ultrasound diagnosis apparatus according to the present invention will be specifically described below with reference to the drawings.

Figure 1:
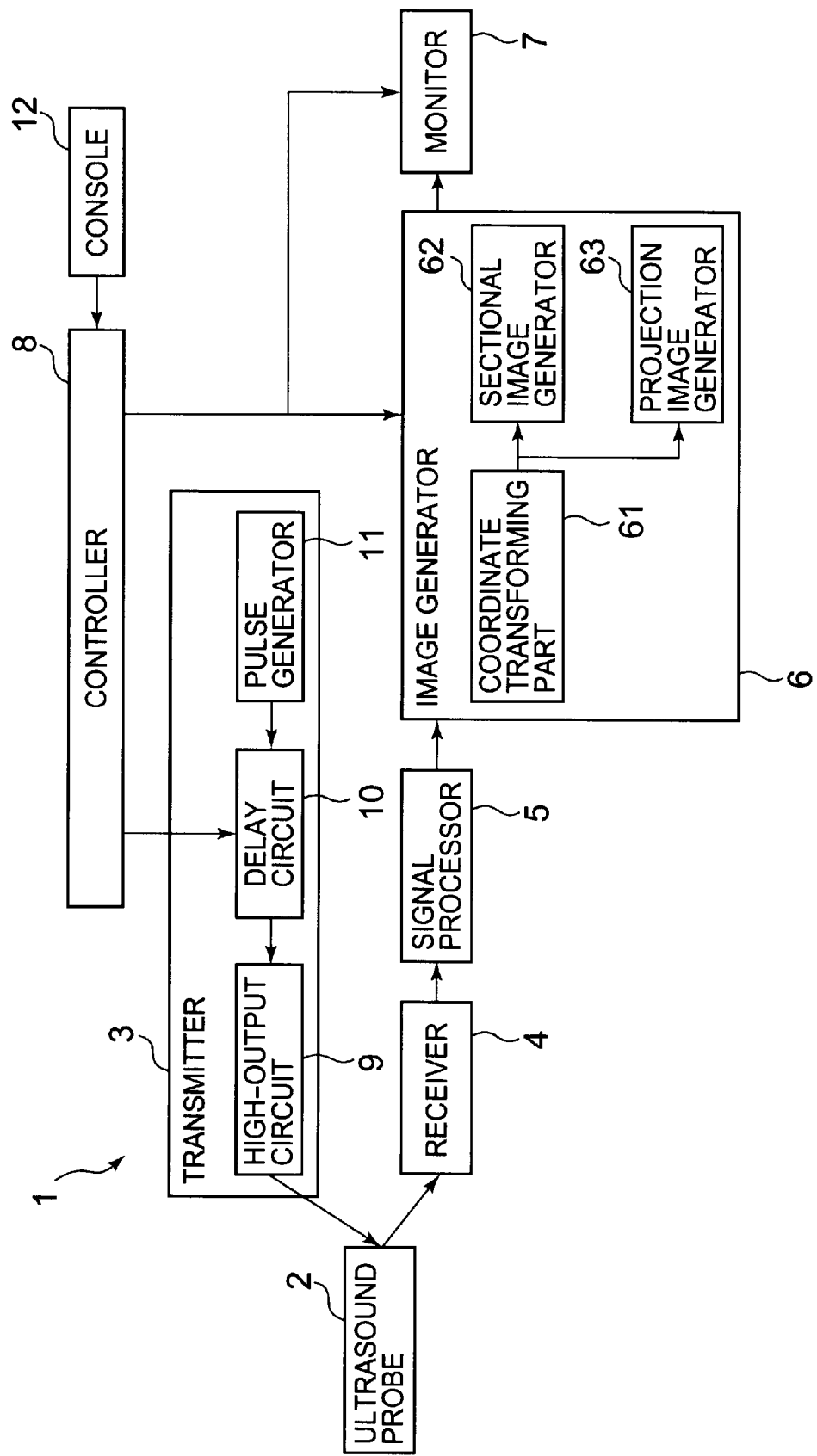
FIG. 1 illustrates the configuration of an ultrasound diagnosis apparatus according to this embodiment.
Figure 2:
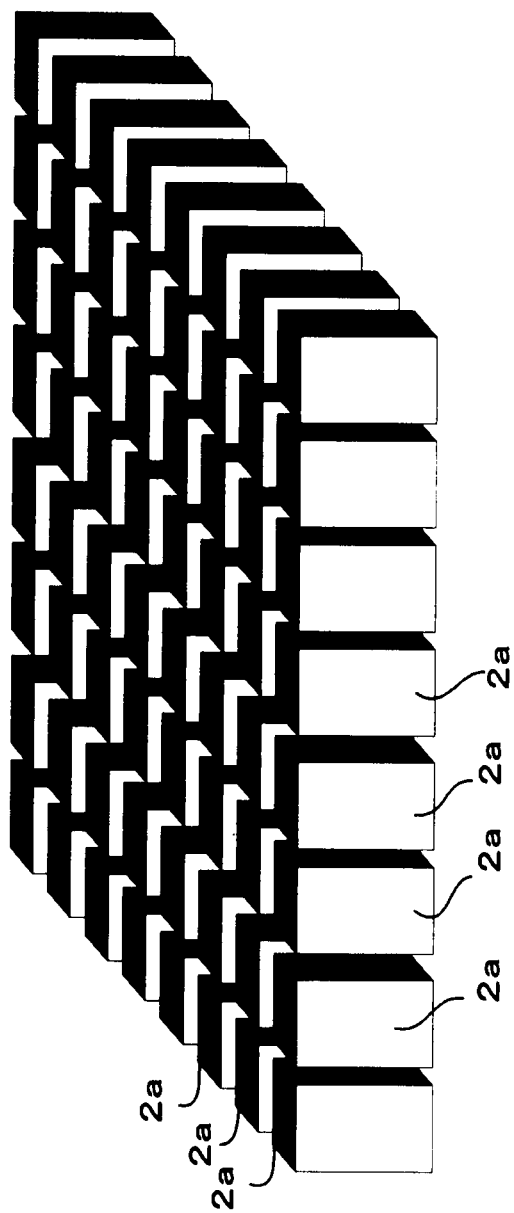
FIG. 2 illustrates piezoelectric elements arranged two-dimensionally.

FIG. 1 is a block diagram illustrating the configuration of an ultrasound diagnosis apparatus according to this embodiment. FIG. 2 is a schematic view illustrating piezoelectric elements of an ultrasound probe. As shown in FIG. 1, an ultrasound diagnosis apparatus 1 of this embodiment is connected to an ultrasound probe 2 capable of three-dimensional scan. This ultrasound diagnosis apparatus 1 causes the ultrasound probe 2 to transmit and receive ultrasonic waves to and from inside the body of a subject, generates an image of the inside of the subject based on the received ultrasonic waves, and causes a monitor 7 to display this image so as to be visually recognizable. In particular, this ultrasound diagnosis apparatus 1 three-dimensionally transmits and receives ultrasonic waves to and from the inside of the subject, generates volume data continuously in a chronological order, and displays a three-dimensional moving image.

As shown in FIG. 2, the ultrasound probe 2 has a configuration in which a plurality of piezoelectric elements 2a are two-dimensionally arranged.

The piezoelectric elements 2a are composed of a ceramic material, such as lead zirconate titanate (Pb(Zr,Ti)O3), lithium niobate (LiNbO3), barium titanate (BaTiO3), and lead titanate (PbTiO3). The piezoelectric element 2a is an acoustic/electric reversible conversion element, and oscillates ultrasonic waves when pulse signals are applied thereto, and outputs echo signals in accordance with the intensity of the ultrasonic waves when receiving the ultrasonic waves. An image of the inside of the subject is visualized by processing the echo signals in the ultrasound diagnosis apparatus 1. The ultrasound probe 2 in which the plurality of piezoelectric elements 2a are two-dimensionally arranged transmits and receives ultrasonic waves three-dimensionally, and receives volume data radiating from the surface of the ultrasound probe 2, as the echo signals.

The ultrasound diagnosis apparatus 1 has a transmitter 3, a receiver 4, a signal processor 5, an image generator 6, a monitor 7, a controller 8, and a console 12. The transmitter 3 and the receiver 4 are connected to the ultrasound probe 2. The image generator 6 has a coordinate transforming part 61, a sectional image generator 62, and a projection image generator 63.

The transmitter 3 is a transmission controller that generates pulse signals and applies the pulse signals to the piezoelectric elements 2a, thereby controlling a region scanned with ultrasonic waves. The transmitter 3 has a pulse generator 11, a delay circuit 10, and a high-output circuit 9.

The pulse generator 11 is a circuit that generates pulse signals. The pulse generator 11 internally has a clock generator that generates primitive signals and, based on the frequency of the primitive signals, outputs pulse signals with a frequency represented by preset frequency data. The delay circuit 10 is a circuit that delays the pulse signals generated by the pulse generator 11 for each of the piezoelectric elements 2a. The delay circuit 10 generates a delay based on preset delay data. For example, when a longer delay is applied to the piezoelectric elements 2a arranged on one side, ultrasonic beams are focused on the other side. In other words, the ultrasonic beams are oscillated within a scanning range in the main scanning direction in the delay sequence by the pulse generator 11. The high-output circuit 9 converts the delayed pulse signals into high voltage, and applies it to the piezoelectric elements 2a. The scanning range in the secondary scanning direction changes the line of the piezoelectric elements 2a to which the high voltage is applied.

The receiver 4 receives an echo signal at each focal point within a scanning region from the ultrasound probe 2. This receiver 4 amplifies the echo signals and converts them into digital signals. Moreover, the receiver 4 applies a delay time necessary for determining reception directionality to the echo signals outputted from the respective piezoelectric elements 2a, performs phasing addition, and generates a single echo signal in which reflection components from a direction according to the reception directionality are enhanced. The receiver 4 outputs the processed echo signal to the signal processor 5.

The signal processor 5 visualizes amplitude information of the echo signals at the respective focal points within the scanning region, and generates B-mode volume data from all of them. The volume data is a collection of echo signals at the respective focal points within the scanning region. More specifically, a band-pass filter process is executed on the echo signals outputted from the receiver 4, and then the envelope curve of the output signals is detected. The detected data is compressed by logarithmic transformation.

The image generator 6 executes an MPR process on the volume data to generate a sectional image, and renders the volume data to generate a projection image.

Figure 3:
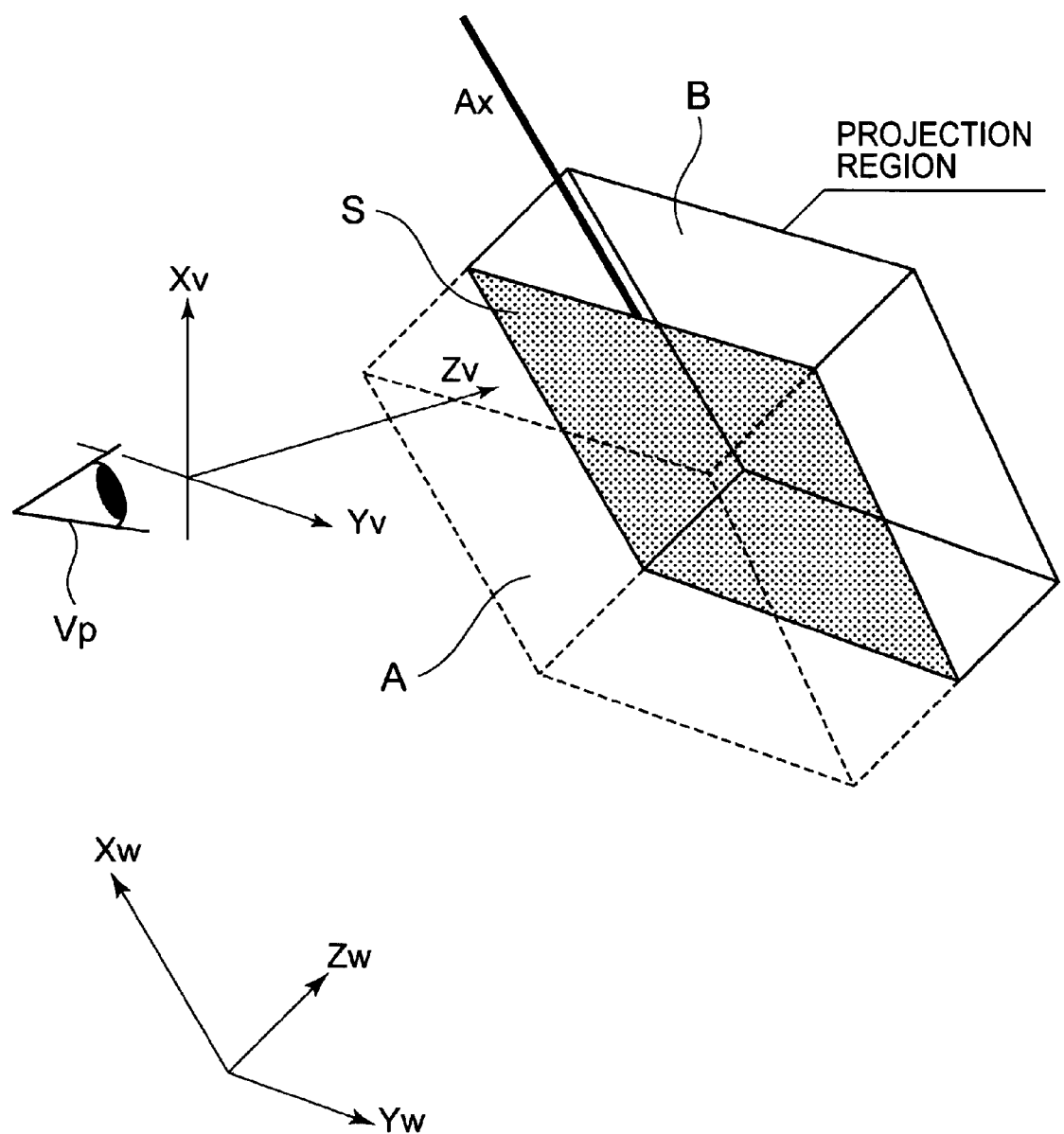
FIG. 3 illustrates an aspect of generating an image.

FIG. 3 is a view illustrating an aspect of generating an image by the generator 6. The coordinate transforming part 61 is a digital scan converter, which executes, on the volume data, modeling transformation to the world coordinate system (Xw, Yw, Zw) and the viewing coordinate system (Xv, Yv, Zv) that are represented by orthogonal coordinates. The world coordinate system is a coordinate system that defines the entire three-dimensional space.

The viewing coordinate system is a coordinate system for rendering in which a viewpoint Vp is the original point and a direction looking from the viewpoint Vp is the Z axis. The positional relationship of the viewing coordinate system with the world coordinate system is previously defined.

When the viewpoint Vp is changed by using the console 12, or the viewpoint Vp is changed in conjunction, the coordinate transforming part 61 re-defines the relationship between the changed viewpoint coordinate system and the world coordinate system by modeling transformation.

The volume data is acquired in a local coordinate system. The local coordinate system is three dimensions represented by a distance and two angles. The distance is a distance between the position of the ultrasound probe 2 and the focal point. One of the angles is an angle in the main scanning direction formed between the axis Ax extending in the depth direction from the center of gravity of the two-dimensional arrangement of the piezoelectric elements 2a and the line extending from the center of gravity to the focal point. The other angle is an angle in the secondary scanning direction formed between the abovementioned lines. The coordinate transforming part 61 executes, on the volume data acquired in the local coordinate system, modeling transformation to the world coordinate system (Xw, Yw, Zw). Furthermore, the coordinate transforming part 61 executes, on the volume data of the world coordinate system, modeling transformation to the viewing coordinate system.

The sectional image generator 62 is a first image generator that executes section conversion on a reference cross section S of the volume data by the MPR process and generates a sectional moving image (hereinafter referred to as an S-sectional moving image Ds) in the world coordinate system. The reference cross section S is predefined. For example, the reference cross section S may be a plane in the main scanning direction including the axis Ax extending in the depth direction from the center of gravity of the two-dimensional arrangement of the piezoelectric elements 2a.

The sectional image generator 62 sequentially generates frame data of the S-sectional moving image Ds in which the voxel values of voxels arranged on the plane are two-dimensionally arranged, for each of the volume data sequentially generated.

The projection image generator 63 is a second image generator that performs projection transformation by rendering with a previously sectioned region A or B of a space represented by volume data as a projection region and generates a projection image (hereinafter referred to as an S-side projection moving image Dp) in the viewing coordinate system. The space is sectioned into the regions by the reference cross section S. The rendering by the projection image generator 63 may be volume rendering, for example. The volume rendering is so-called transmission projection transformation, which is a method of calculating the transmission of light in accordance with opacity and reflection to the viewpoint Vp and sequentially generating frame data of the S-side projection moving image Dp while shading. In other words, a side closer to the viewpoint Vp is reflected more on the S-side projection moving image Dp.

The viewpoint Vp and the projection region in rendering are determined in accordance with the positional relationship between the reference cross section S and the region A or B to be rendered. More specifically, the projection image generator 63 sets the region A or B positioned on the back of the reference cross section S when viewed from the viewpoint Vp, as the projection region. Alternatively, the projection image generator 63 places the viewpoint Vp on the back of the reference cross section S when viewed from the projection region. In other words, rendering is performed so that the reference cross section S side is reflected more on the S-side projection moving image Dp. For example, when one side is the region A and the other side is the region B across the reference cross section S and the viewpoint Vp is set on the region A side, the region B that is on the back of the reference cross section S when viewed from the viewpoint Vp becomes the projection region. The projection image generator 63 determines the viewpoint Vp or the projection region in accordance with the positional relationship in the world coordinate system between the viewpoint Vp and the reference cross section S.

That is to say, assuming volume data is placed at a position that does not include the original point of the world coordinate system, if the viewpoint Vp is on the side of the original point of the world coordinate system from the reference cross section S, a region on the back of the reference cross section S in the world coordinate system will be regarded as the projection region. If the reference cross section S is on the side of the original point of the world coordinate system from the viewpoint Vp, a region on the original point side from the reference cross section S in the world coordinate system will be regarded as the projection region. If the region on the original point side from the reference cross section S in the world coordinate system is the projection region, the viewpoint Vp is placed on the back of the reference cross section S in the world coordinate system. If a region on the back of the reference cross section S in the world coordinate system is the projection region, the viewpoint Vp is placed on the original point side from the reference cross section S in the world coordinate system. In change of the viewpoint Vp, it is moved axisymmetrically about the axis Ax extending in the depth direction from the center of gravity of the two-dimensional arrangement of the piezoelectric elements 2a.

The sectional image generator 62 executes section transformation by the MPR process on a cross section intersecting the projection region among planes that are orthogonal to the reference cross section S and along the axis Ax extending in the depth direction from the center of gravity of the two-dimensional arrangement of the piezoelectric elements 2a, and generates a sectional image (hereinafter referred to as a T-sectional moving image Dt).

The controller 8 includes a CPU (central processing unit) and controls the delay circuit 10, the image generator 6 and the monitor 7 in response to an operation of the console 12. The console 12 is a keyboard or a trackball and is an operation part through which it is possible to input rotation of the viewpoint Vp or change of the projection region. The monitor 7 is a display such as an LCD (liquid crystal display) and a CRT (cathode ray tube), and displays a sectional image and a projection image generated by the image generator 6.

Figure 4:
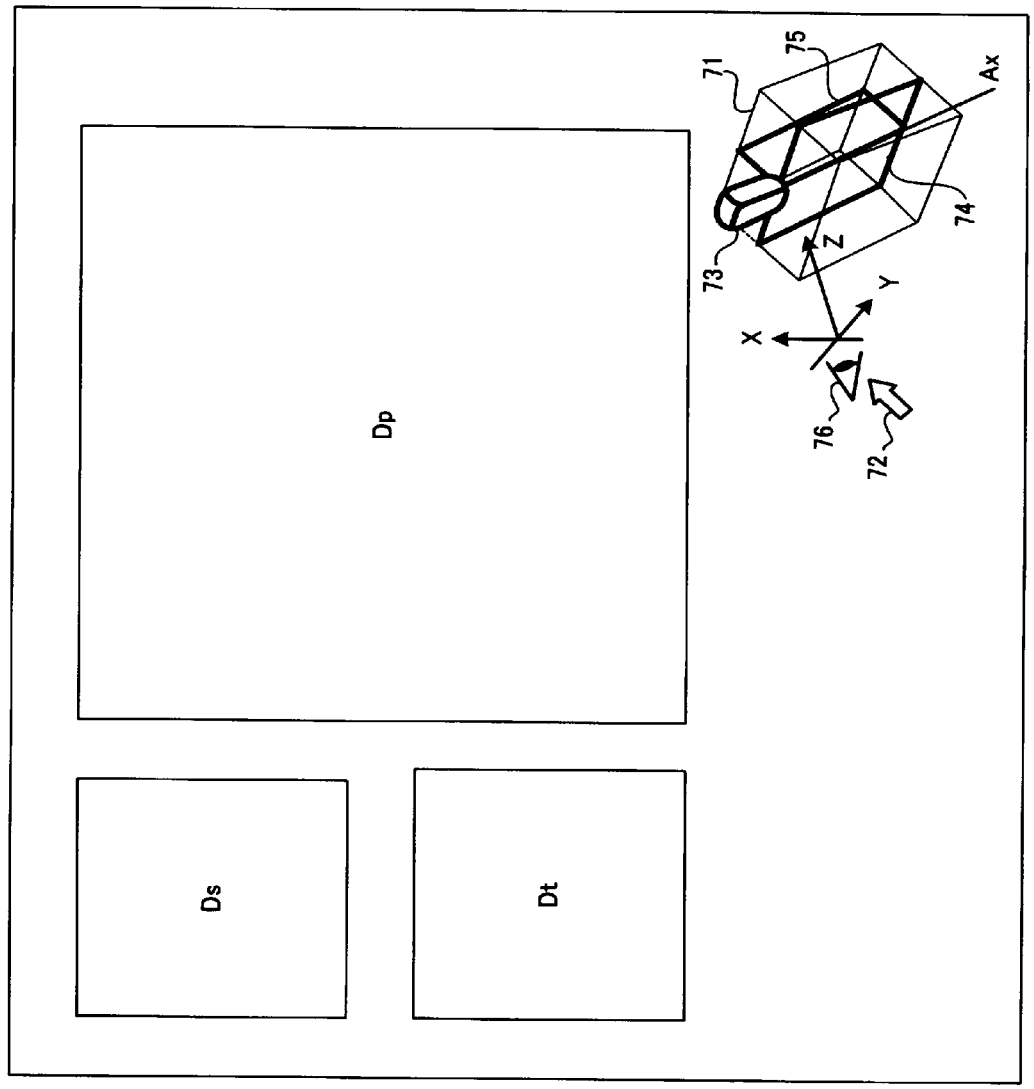
FIG. 4 illustrates a display screen that displays a tomographic image and a projection image.

FIG. 4 is a schematic view illustrating a display screen that displays a tomographic image and a projection image. The S-sectional moving image Ds, the T-sectional moving image Dt, and the S-side projection moving image Dp generated by the image generator 6 are displayed on the monitor 7. Further, a scannable range frame 71 representing a range that can be scanned by the ultrasound probe 2 is displayed together with a cursor 72 on the screen. In the scannable range frame 71, a probe object 73 of the ultrasound probe 2, an S-section frame 74 representing the S-sectional moving image Ds, a T-section frame 75 representing the T-sectional moving image Dt and a viewpoint object 76 of the viewpoint Vp show the positional relationship of the ultrasound probe 2, the S-sectional moving image Ds, the T-sectional moving image Dt, the S-side projection moving image Dp and the viewpoint Vp. A region including the T-section frame 75 is a projection region to be projected as the S-side projection moving image Dp.

Figure 5:
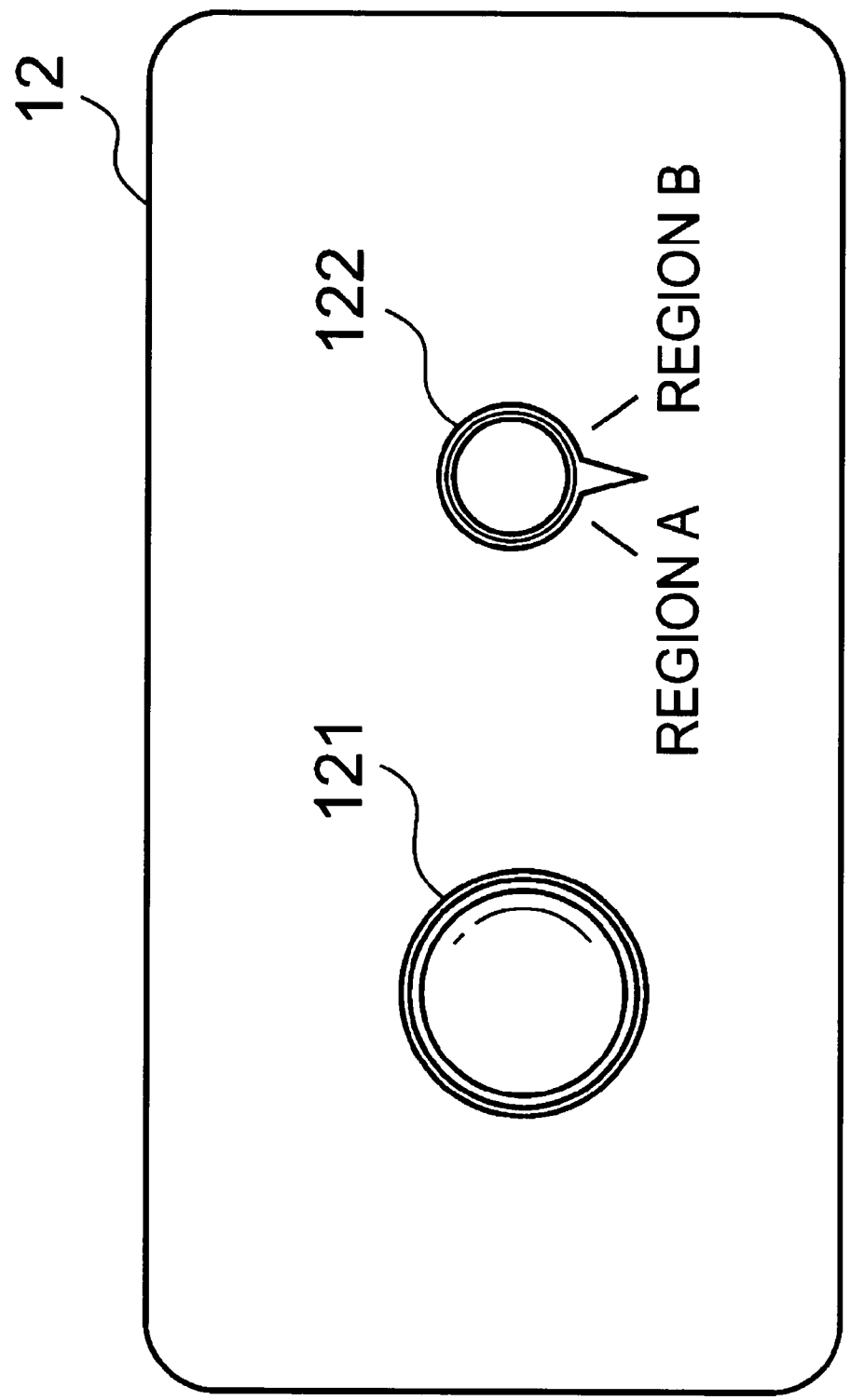
FIG. 5 illustrates a console.

FIG. 5 is a schematic view illustrating the console 12. The console 12 is an operation part to which a trackball 121 and a knob 122 are attached.

When the trackball 121 is rotated, the controller 8 causes the cursor 72 displayed on the monitor 7 to move. When the cursor 72 is put on the viewpoint object 76 and the trackball 121 is rotated while being pressed, the controller 8 changes the display position of the viewpoint object 76. The controller 8 changes the display position of the viewpoint object 76 so as to axially rotate or axially move around the axis Ax of the modeling coordinate system extending in the depth direction from the center of gravity of the two-dimensional arrangement of the piezoelectric elements 2a. Moreover, the knob 122 is a switch for changing the projection region. For example, the knob 122 can be switched between positions for selecting the region A and the region B adjacent to each other across the reference cross section S. When the knob 122 is switched to the region A, the controller 8 controls to display the T-section frame 75 so as to cross the region A. When the knob 122 is switched to the region B, the controller 8 controls to display the T-section frame 75 so as to cross the region B. Moreover, the controller 8 outputs, to the image generator 6, a signal representing the position coordinate of the changed viewpoint Vp in the world coordinate system or a signal representing the switched projection region.

Figure 6:
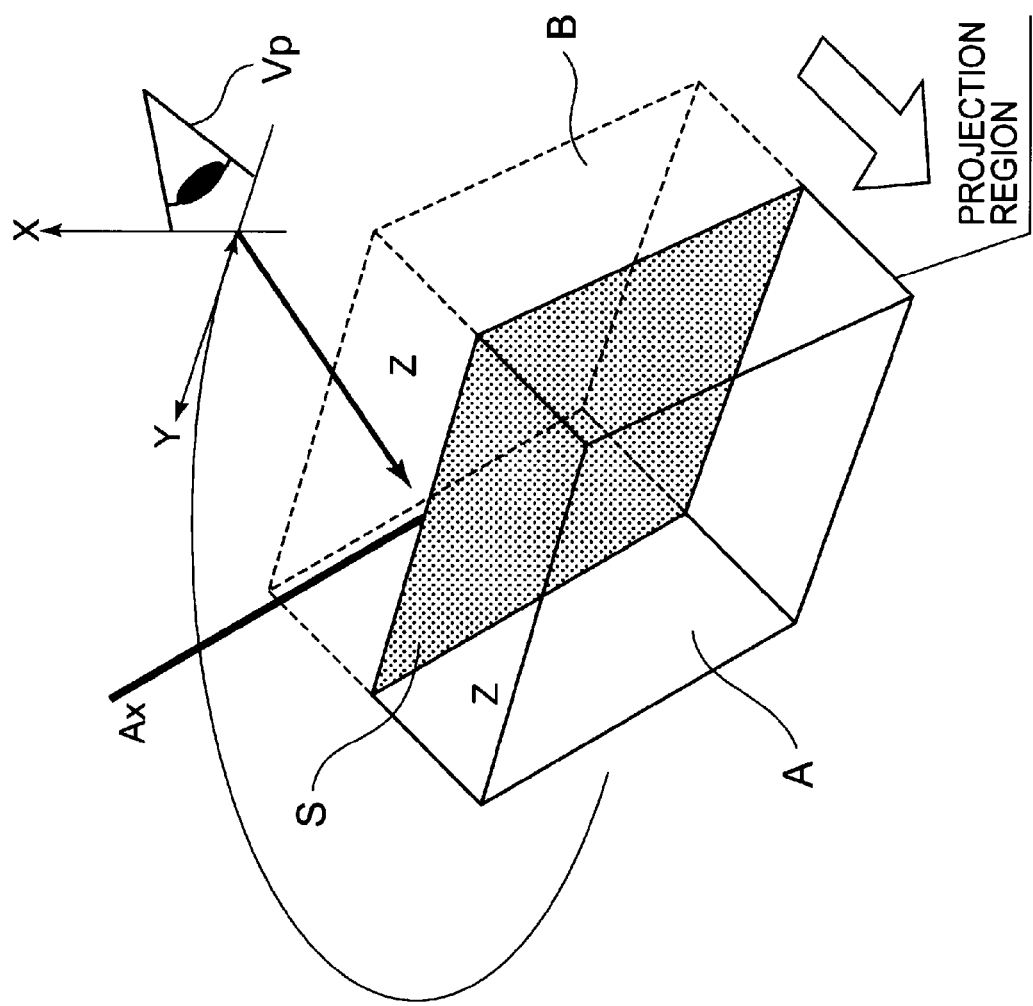
FIG. 6 illustrates an aspect of re-generating an image in response to an operation of changing a viewpoint or an operation of switching a projection region.

FIG. 6 is a schematic view illustrating an aspect of re-generating an image in response to the operation of changing the viewpoint Vp or the operation of switching the projection region by the image generator 6. When the position of the viewpoint Vp is changed, the projection image generator 63 generates the S-side projection moving image Dp with the region A or B as the projection region, which exists on the back of the reference cross section S when viewed from the viewpoint Vp. In other words, the projection image generator 63 samples a group of voxel data of the region A or B existing on the back of the reference cross section S when viewed from the changed viewpoint Vp, calculates the transmission of light in accordance with opacity and reflection to the changed viewpoint Vp, and sequentially generates frame data of the S-side projection moving image Dp while shading.

More specifically, the projection image generator 63 compares the position of the viewpoint Vp with the position of the reference cross section S in the world coordinate system and, if the viewpoint Vp is positioned on the original point side from the reference cross section S in the world coordinate system, the S-side projection moving image Dp is generated with the region B as the projection region, which exists on the back of the reference cross section S. On the other hand, if the viewpoint Vp is positioned on the back of the reference cross section S in the world coordinate system, the S-side projection moving image Dp is generated with the region A as the projection region, which exists on the original point side from the reference cross section S. Here, modeling transformation is executed on the volume data as the absolute location of the world coordinate system defined beforehand.

Therefore, the projection image generator 63 may be configured to previously store range information of the world coordinate system of the viewpoint Vp and a coordinate range in the world coordinate system of the region set as the projection region in combination and render by sampling the group of voxel data in the coordinate range combined with the range to which the viewpoint Vp after the change belongs.

Further, when the projection region is switched, the projection image generator 63 moves the viewpoint Vp so that the projection region exists on the back of the reference cross section S when viewed from the viewpoint Vp, and generates the S-side projection moving image Dp. In other words, the projection image generator 63 samples the group of voxel data of the region A or B existing on the back of the reference cross section S when viewed from the original point after the coordinate transformation, i.e., from the changed viewpoint Vp, calculates the transmission of light in accordance with opacity and reflection to the changed viewpoint Vp, and sequentially generates frame data of the S-side projection moving image Dp while shading.

More specifically, the projection image generator 63 compares the position of the projection region with the position of the viewpoint Vp in the world coordinate system. If the viewpoint Vp and the projection region are on the same side with respect to the reference cross section S as a result of the comparison, the coordinate transforming part 61 changes the position of the viewpoint Vp axisymmetrically about the axis Ax extending in the depth direction from the center of gravity of the two-dimensional arrangement of the piezoelectric elements 2a, and then the projection image generator 63 renders the projection region from the side of the changed viewpoint Vp.

Here, modeling transformation is executed on the volume data as the absolute location of the world coordinate system determined beforehand.

Therefore, the projection image generator 63 may be configured to render by previously associating the combination of the range information of the world coordinate system of the viewpoint Vp and the coordinate range in the world coordinate system of the region set as the projection region with a switch of the knob 122, and sampling the group of voxel data in the switched coordinate range.

Thus, when the viewpoint Vp is changed, the image generator 6 changes the projection region to be rendered in conjunction therewith and thereafter executes re-rendering. Moreover, when the projection region is changed, the image generator 6 changes the viewpoint Vp in conjunction therewith and thereafter executes re-rendering. In other words, in order to execute rendering in a state that the reference cross section S is always in front of the viewpoint Vp, if the viewpoint Vp is changed beyond the reference cross section S, the image generator 6 changes the projection region in conjunction therewith and thereafter executes rendering, whereas if the projection region is changed beyond the reference cross section S, the image generator 6 changes the viewpoint Vp in conjunction therewith and thereafter executes rendering.

Figure 7:
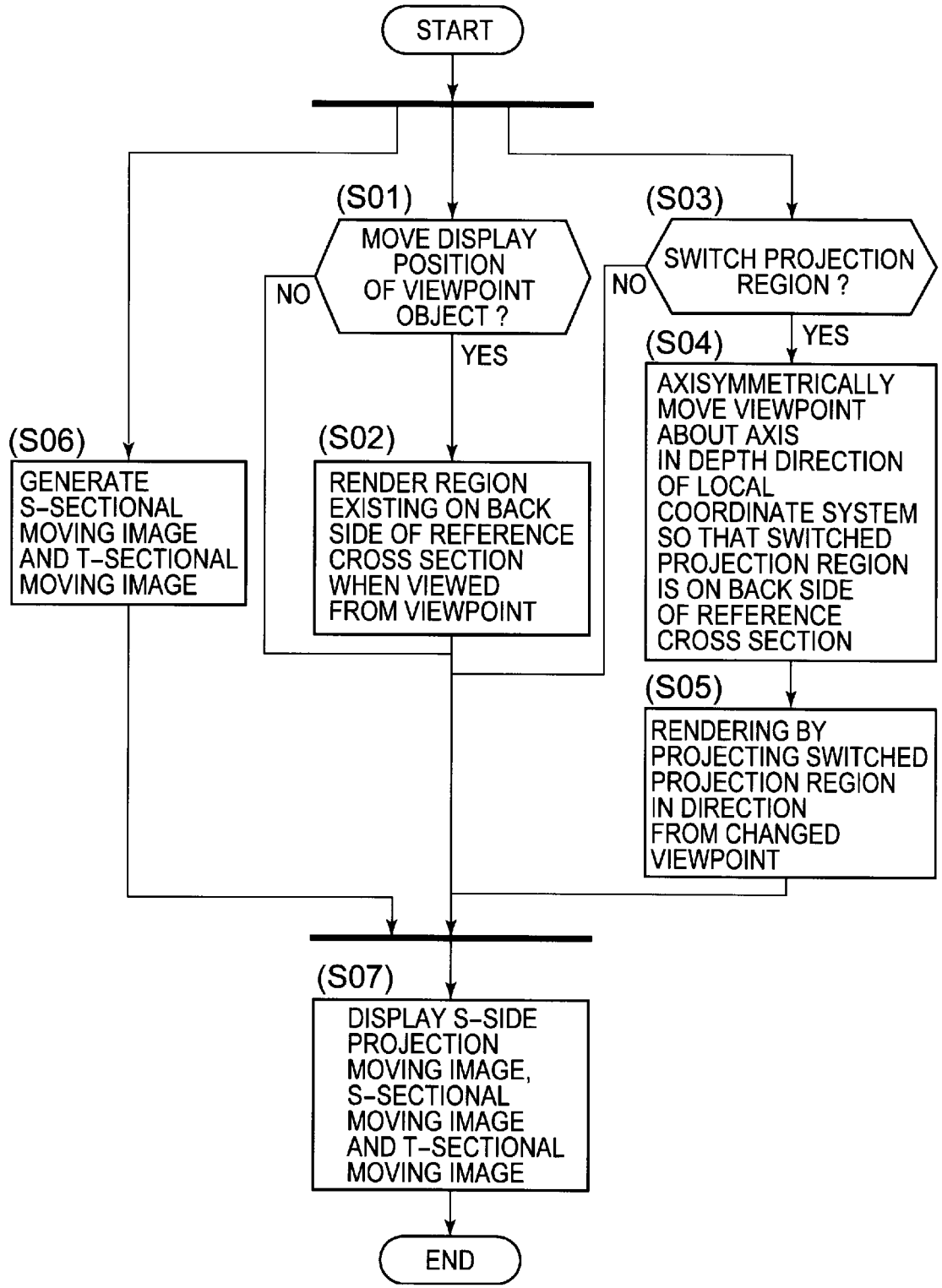
FIG. 7 illustrates a flow chart showing an operation of changing a viewpoint and a projection region in conjunction and re-rendering by the ultrasound diagnosis apparatus.

FIG. 7 is a flow chart illustrating the operation of the ultrasound diagnosis apparatus 1 for changing the viewpoint Vp and the projection region in conjunction and executing re-rendering. When the display position of the viewpoint object 76 is moved by operating the trackball 121 of the console 12 (S01, Yes), the projection image generator 63 sequentially generates frame data of the S-side projection moving image Dp with the region A or B as the projection region, which exists on the back of the reference cross section S when viewed from the viewpoint Vp (S02).

Further, when the projection region is switched by operating the knob 122 of the console 12 (S03, Yes), the coordinate transforming part 61 moves the viewpoint Vp axisymmetrically about the axis Ax so that the switched projection region is on the back of the reference cross section S (S04), and the projection image generator 63 projects the switched projection region in a direction from the changed viewpoint Vp and sequentially generates frame data of the S-side projection moving image Dp (S05).

In parallel with the generation of the S-side projection moving image Dp in S02 and S05, the sectional image generator 62 sequentially generates frame data of the S-sectional moving image Ds and the T-sectional moving image Dt (S06). The controller 8 then causes the monitor 7 to display the generated S-side projection moving image Dp, S-sectional moving image Ds and T-sectional moving image Dt (S07).

The explanation of the abovementioned ultrasound diagnosis apparatus 1 described above is given on the assumption that the entire scannable range is scanned. Alternatively, the ultrasound diagnosis apparatus may be configured to transmit and receive ultrasonic waves with part of the scannable range as a scanning region, which can be switched, and change the projection region and the viewpoint Vp in conjunction with the switch. Below, an ultrasound diagnosis apparatus 1 in which part of the scannable range is a scanning region and the scanning region is switchable will be described.

The knob 122 is a switch for changing a scanning region. For example, the knob 122 is switchable between positions to select the region A or the region B adjacent to each other across the reference cross section S. When the knob 122 is switched to the region A, the controller 8 transmits delay data for scanning the region A to the transmitter 3, displays the T-section frame 75 so as to cross the region A, and outputs signals representing the switched projection region to the image generator 6. When the knob 122 is switched to the region B, the controller 8 transmits delay data for scanning the region B to the transmitter 3, displays the T-section frame 75 so as to cross the region B, and outputs signals representing the switched projection region to the image generator 6. The trackball 121 is an operation part for changing the viewpoint Vp. When the cursor 72 is put on the viewpoint object 76 and the trackball 121 is rotated while being pressed, the controller 8 changes the display position of the viewpoint object 76 with reference to the axis Ax.

Moreover, based on the positional relationship between the changed viewpoint Vp and the scannable range in the world coordinate system, the controller 8 determines whether the region having a relationship in which the reference cross section S is in front of the viewpoint Vp is the region A or B, and transmits the delay data associated with the relevant region to the transmitter 3. This determination is the same as the process by the projection image generator 63, and a common program or a common circuit may be used in configuration.

In the transmitter 3, the pulse generator 11 changes the scanning region to a switched region by generating a delay in accordance with the given delay data, or changes the scanning region to a region in which the reference cross section S is in front of the viewpoint Vp in conjunction with the change of the viewpoint Vp. The image generator 6 executes a rendering process of projecting, in a direction from the viewpoint Vp, the scanning region determined to have a relationship that the reference cross section S is in front of the viewpoint Vp based on the positional relationship between the switched scanning region or the changed viewpoint Vp and the scannable range in the world coordinate system, thereby generating the S-side projection moving image Dp.

Here, a combination of delay data representing the scanning region, range information of the world coordinate system of the viewpoint Vp, and the coordinate range in the world coordinate system of a region set as the projection region may be previously associated with the switch of a knob 122.

Figure 8:
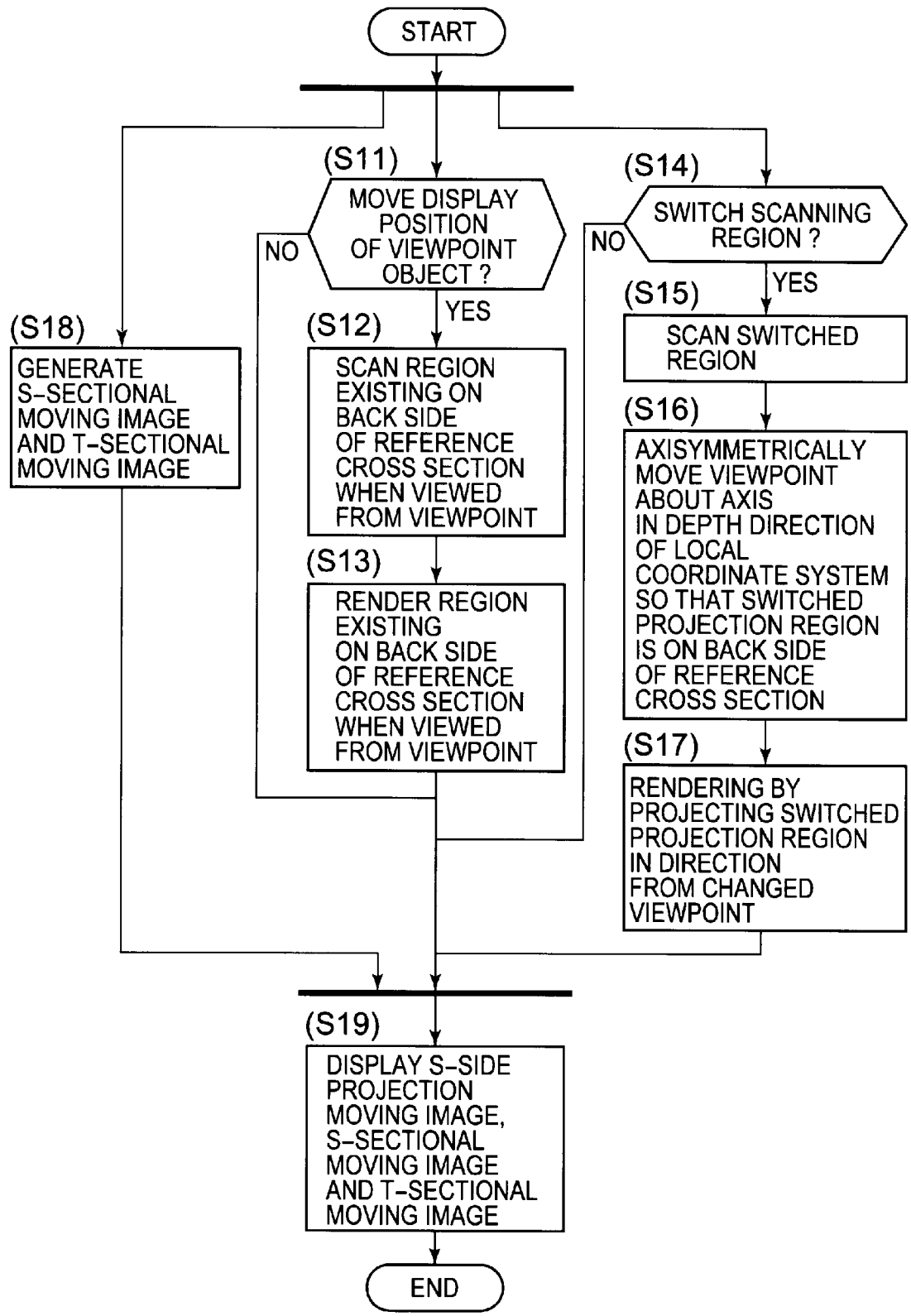
FIG. 8 illustrates a flow chart showing an operation of changing a scanning region and re-rendering.

FIG. 8 is a flow chart illustrating the operation of changing the scanning region and re-rendering in the ultrasound diagnosis apparatus 1 capable of switching part of the scannable range as the scanning region.

When the trackball 121 of the console 12 is operated and the display position of the viewpoint object 76 is moved (S11, Yes), the controller 8 transmits delay data in which the region A or B existing on the back of the reference cross section S when viewed from the viewpoint Vp is the scanning region, to the transmitter 3, and causes it to transmit and receive ultrasonic waves to and from this scanning region (S12). The projection image generator 63 sequentially generates frame data of the S-side projection moving image Dp with the region A or B existing on the back of the reference cross section S when viewed from the viewpoint Vp as the projection region (S13).

Further, when the knob 122 of the console 12 is operated and the scanning region is switched (S14, Yes), the controller 8 transmits delay data associated with the position of the knob 122 to the transmitter 3, and causes it to transmit and receive ultrasonic waves to and from the scanning region (S15). The coordinate transforming part 61 moves the viewpoint Vp axisymmetrically about the axis Ax so that the switched scanning region is on the back of the reference cross section S (S16), and the projection image generator 63 projects the switched projection region in a direction from the changed viewpoint Vp and sequentially generates frame data of the S-side projection moving image Dp (S17).

In parallel with the generation of the S-side projection moving image Dp in S13 and S17, the sectional image generator 62 sequentially generates frame data of the S-sectional moving image Ds and the T-sectional moving image Dt (S18). The controller 8 then causes the monitor 7 to display the generated S-side projection moving image Dp, S-sectional moving image Ds and T-sectional moving image Dt (S19).

Figure 9:
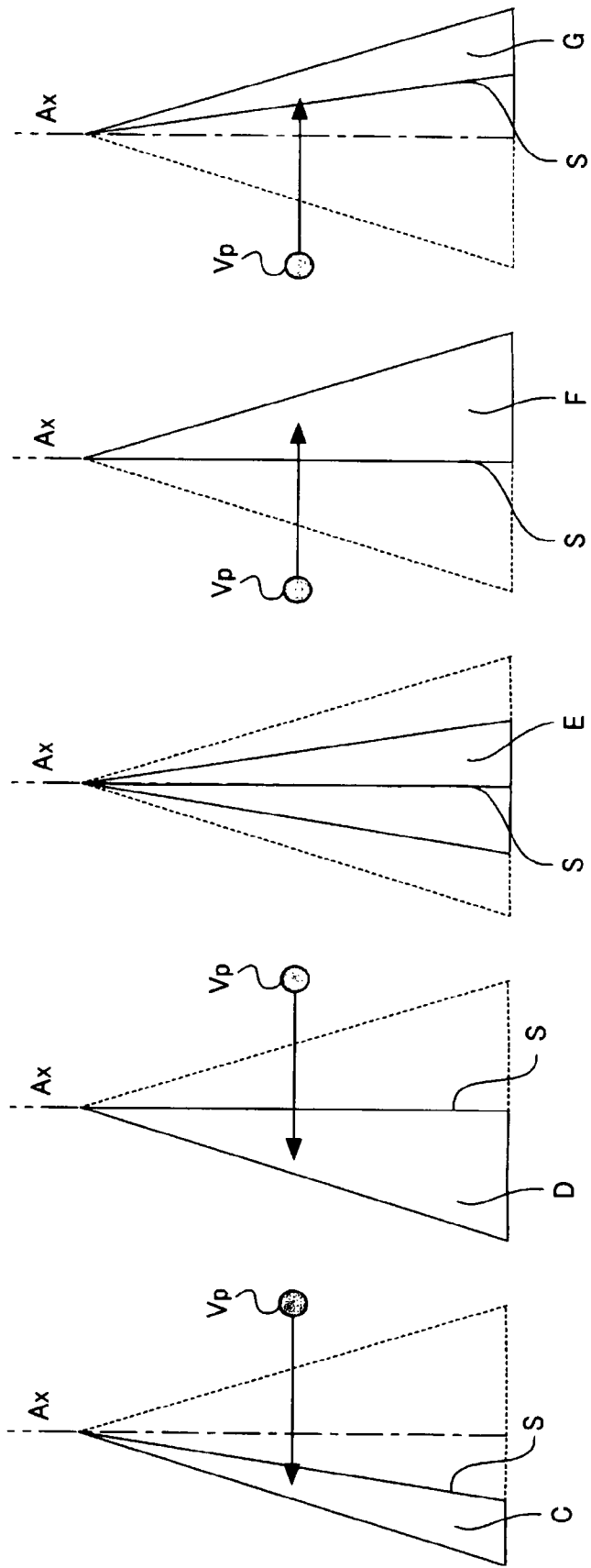
FIG. 9 illustrates an example of sectioning of a scanning region or a projection region viewed from a secondary scanning direction.

Although the sections of the scanning region or projection region to be changed are the region A and the region B in the above embodiment, it is also possible to section into more regions in accordance with the position of the knob 122. FIG. 9 is a schematic view taken from the secondary scanning direction, illustrating an example of sectioning of the scanning region or the projection region.

For example, as shown in FIG. 9, the scanning region or projection region is sectioned into five regions C, D, E, F and G including overlapping regions, and each of them is associated with a position of the knob 122. For each of the regions C, D, E, F and G, a reference cross section S is previously defined. The regions C, D, F and G are regions that do not include the axis Ax, and the reference cross sections S thereof are set on the boundary planes of the regions close to the axis Ax. The region E is a region including the axis Ax, and the reference cross section S thereof is a plane including the center of this region, i.e., including the axis Ax.

Further, for each of the regions C, D, E, F and G, a viewpoint Vp is previously defined so that the reference cross section S is in front and each of the regions C, D, E, F and G is on the back. That is to say, the controller 8 previously stores delay data for scanning the regions C, D, E, F and G, and outputs the delay data of the region C, D, E, F or G to the transmitter 3 in accordance with the position of the knob 122. The sectional image generator 62 previously stores information representing the position of the reference cross section S in association with the position of the knob 122. Moreover, the projection image generator 63 previously stores positional information of the viewpoint Vp in association with the position of the knob 122. For example, it is assumed that the scanning region or projection region is switched sequentially from the region E in the order of F, G, F, E, D, C, D, E in FIG. 9. In this case, rendering is executed in the same direction from the viewpoint Vp for the regions F, G, F, E. Then, when the region is switched to the region D, the viewpoint Vp is moved axisymmetrically about the axis Ax and directed reversely, and rendering is executed. Moreover, while the region is changed from the region D in the order of C, D, E, rendering is executed without change of the viewpoint Vp having been directed reversely.

Thus, in the ultrasound diagnosis apparatus 1, in conjunction with change of the projection region, the viewpoint Vp is changed to a position that the reference cross section S is in front and the changed projection region is on the back, and then the changed projection region is rendered and an image is displayed. Furthermore, in the ultrasound diagnosis apparatus 1, in conjunction with change of the viewpoint Vp, the projection region is changed to the region A or B in which the reference cross section S is in front and the changed viewpoint Vp is on the back, a rendering process of projecting the projection region in a direction from the changed viewpoint Vp is executed, and an image is displayed on the monitor 7. Consequently, it is possible to maintain an aspect of rendering at the viewpoint Vp with the viewpoint Vp having the reference cross section S in front of the projection region without executing a number of complicated operating procedures, e.g., the operation of adjusting the projection region after the operation of adjusting the viewpoint Vp and vice versa. Therefore, it becomes easier to grasp a steric structure, thereby enhancing the efficiency of observation of the inside of a subject.

Change of the viewpoint Vp in conjunction with the change of the projection region may be change around the axis Ax in the depth direction in the local coordinate system of the volume data. Alternatively, in the operation of changing the viewpoint Vp, the change may be regulated to a range around the axis Ax. Consequently, even if a projection region is changed, the tilt of the projection region to be observed would not change from above to below or from below to above.

Further, in the ultrasound diagnosis apparatus 1, in conjunction with change of the scanning region, the viewpoint Vp is changed to a position where the reference cross section S is in front and the projection region is on the back, and then the changed projection region is rendered and a image is displayed. Furthermore, in the ultrasound diagnosis apparatus 1, in conjunction with change of the viewpoint Vp, the scanning region is changed to the region A or B where the reference cross section S is in front and the changed viewpoint Vp is on the back, and then a rendering process of projecting the relevant scanning region in the direction of the changed viewpoint Vp is executed and an image is displayed on the monitor 7.

Consequently, it is possible to maintain an aspect of rendering at the viewpoint Vp with the reference cross section S in front of the projection region, without executing a number of complicated changing operation steps, e.g., executing an operation of positioning the viewpoint Vp and an operation of changing the projection region after an operation of changing the scanning region, or executing an operation of changing the scanning region and the projection region after an operation of changing the viewpoint Vp. As a result, it becomes easier to grasp a steric structure, and the efficiency of observation of the inside of a subject increases.

Although the reference cross section S is previously set at a predetermined position in the above embodiment, an arbitrary cross section may be designated as the reference cross section S by an operation through the console 12. The sectional image generator 62 generates the S-sectional moving image Ds by executing the MPR process on the designated cross section. The projection image generator 63 places the designated reference cross section S in front of the viewpoint Vp and generates the S-side projection moving image Dp with the region existing on the back as the projection region.

Further, although an example that the S-sectional moving image Ds and the T-sectional moving image Dt are simultaneously displayed on the screen is described in the above embodiment, only one of the above images may be displayed. In the case of displaying only one of the above images, the image generator 6 may generate only a sectional moving image to be displayed. Moreover, although an example that these sectional moving images and the S-side projection moving image Dp are simultaneously displayed is described in the above embodiment, it is possible to configure to first display only the sectional moving image and then display the S-side projection moving image Dp. In other words, the term "display" includes display of both the images at one time as well as display of each of the images at different times.

Although the two-dimensional array type with the piezoelectric elements 2a two-dimensionally arranged is described above as the ultrasound probe 2 capable of three-dimensional scan, a mechanical 4D type may be used.

The mechanical 4D type ultrasound probe 2 can perform three-dimensional scan by one-dimensionally arranging the piezoelectric elements 2a and mechanically oscillating the arrangement of the piezoelectric elements 2a. Further, for the scan in the main scanning direction, it is possible to employ not only electronic sector scan but also electron linear scan or convex scan.

What is claimed is:

1. An ultrasound diagnosis apparatus that acquires volume data by transmitting and receiving ultrasonic waves to and from an inside of a subject body and generates an image based on the volume data, the ultrasound diagnosis apparatus comprising:
 a first image generator configured to generate a cross sectional image of a designated or predefined reference cross section based on the volume data;
 a second image generator configured to generate a projection image by rendering a predetermined projection region in a direction from a predetermined viewpoint, based on the volume data;
 a display configured to display the cross sectional image generated by the first image generator and the projection image generated by the second image generator;
 an operation part with which change of the projection region is inputted; and
 a determining part configured to determine whether a display position of the predetermined viewpoint moves or not; and wherein
 the second image generator is configured to execute a rendering process for a changed projection region, which exists on the back of the reference cross section from another viewpoint when the display position of the predetermined viewpoint is determined to have been moved, and wherein the second image generator, in conjunction with changing the projection region by the operation part decides a position of the another viewpoint so that the reference cross section is seen in front of the changed projection region inputted by the operation part.

2. The ultrasound diagnosis apparatus according to claim 1, wherein the second image generator changes the predetermined viewpoint around an axis of a depth direction in a local coordinate system of the volume data.

3. The ultrasound diagnosis apparatus according to claim 1, wherein the second image generator changes the predetermined viewpoint when the projection region is changed beyond the reference cross section in the change by the operation part.

4. The ultrasound diagnosis apparatus according to claim 1, wherein the second image generator previously stores information representing the projection region and range information of the predetermined viewpoint, said predetermined viewpoint determined so that the reference cross section is seen in front of the predetermined viewpoint with the projection region existing in back of the reference cross section extending away from the predetermined viewpoint, the information representing the projection region and the range information of the predetermined viewpoint being linked to each other.

5. The ultrasound diagnosis apparatus according to claim 1, wherein the another viewpoint is across the reference cross section from the predetermined viewpoint.

6. An ultrasound diagnosis apparatus that acquires volume data by transmitting and receiving ultrasonic waves to and from an inside of a subject body and generates an image based on the volume data, the ultrasound diagnosis apparatus comprising:

processing circuitry configured to
generate a cross sectional image of a designated or predefined reference cross section based on the volume data,
generate a projection image by rendering a predetermined projection region in a direction from a predetermined viewpoint, based on the volume data,
display the cross sectional image and the projection image,
determine whether a display position of the predetermined viewpoint moves or not,
execute a rendering process for a changed projection region, which exists on the back of the reference cross section from another viewpoint when the display position of the predetermined viewpoint is determined to have been moved, and
decide, in conjunction with changing the projection region, a position of the another viewpoint so that the reference cross section is seen in front of the changed projection region.

* * * * *